United States Patent
Hisanaka et al.

(10) Patent No.: US 6,706,941 B2
(45) Date of Patent: Mar. 16, 2004

(54) ABSORBENT ARTICLE FOR CONTROLLING NORMAL FLORA OF THE SKIN

(75) Inventors: Takayuki Hisanaka, Kagawa-ken (JP); Kiyoshi Miyazawa, Kagawa-ken (JP); Tomoko Endo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/961,861

(22) Filed: Sep. 24, 2001

(65) Prior Publication Data

US 2002/0065496 A1 May 30, 2002

(30) Foreign Application Priority Data

Oct. 11, 2000 (JP) ........................................ 2000-310849

(51) Int. Cl.⁷ ................................................ A61F 13/15
(52) U.S. Cl. ..................................................... 604/360
(58) Field of Search ................................. 604/358, 360

(56) References Cited

U.S. PATENT DOCUMENTS

| | | | |
|---|---|---|---|
| 4,693,713 A | 9/1987 | Chmelir et al. | 604/368 |
| 4,842,593 A | 6/1989 | Jordan et al. | 604/360 |
| 4,883,478 A | 11/1989 | Lerailler et al. | 604/360 |
| 5,518,733 A | 5/1996 | Lamothe et al. | 424/430 |
| 5,607,760 A * | 3/1997 | Roe | 442/375 |

FOREIGN PATENT DOCUMENTS

| | | | |
|---|---|---|---|
| DE | 2 309 575 | 2/1973 | A61K/9/00 |
| DE | 197 13 908 A1 | 4/1997 | A61F/13/20 |
| JP | H2-1265 | 5/1990 | A61F/5/44 |
| WO | 92/13577 | 8/1992 | A61L/15/36 |
| WO | 99/17813 | 4/1999 | A61L/15/36 |
| WO | 99/26635 | 6/1999 | A61K/31/715 |
| WO | 00/61201 | 10/2000 | A61L/15/36 |

* cited by examiner

Primary Examiner—Weilun Lo
Assistant Examiner—C. Lynne Anderson
(74) Attorney, Agent, or Firm—Palmer & Dodge, LLP

(57) ABSTRACT

The present invention relates to an absorbent article such as a disposal diaper, sanitary napkin, or the like which can reduce odor and dermatitis (rash) generated when such an absorbent article is worn. The absorbent article comprises a compound assimilated only by microorganisms in the normal flora of the skin useful and/or harmless to the human body and preferably such a compound assimilated only by microorganisms in normal flora of the skin useful and/or harmless to the human body is glucooligosaccharide.

4 Claims, No Drawings

ABSORBENT ARTICLE FOR CONTROLLING NORMAL FLORA OF THE SKIN

TECHNICAL FIELD

The present invention relates to an absorbent article such as a diaper, sanitary napkin, or the like which can reduce odor and dermatitis (rash) generated when such an absorbent article is worn.

BACKGROUND ART

In recent years, the capacity of absorbent articles such as a disposal diaper, sanitary napkin, and the like to absorb body fluids such as urine and menstrual blood is increasing through improvements to absorbing materials and surface materials. Wearing sensation of absorbent articles has also been greatly improved, resulting in a tendency to extend the period during which the absorbent article is continuously worn.

The habit of wearing compulsory underwear such as a girdle and panty stockings is being established in recent years particularly among women. In addition, a number of women favoring cleanliness wear an absorbent sheet such as a panty liner during periods other than menstrual days. These tendencies result in leaving the skin near the genital organs always under high humidity conditions.

On the other hand, due to continuously wearing absorbent articles such as a disposal diaper and sanitary napkin there is fear that the skin is stimulated by friction and oppression and reduced the resistivity of the skin.

The skin around the area where an absorbent article is worn and the area inside of the absorbent article (hereinafter may be simply referred to as "absorbent article wearing area") are maintained in conditions favorable for the growth of bacteria, not only due to high temperature and high humidity conditions, but also due to the presence of body fluids which are nutrition resources for bacteria. The above-described tendency of continuously wearing absorbent articles provides the absorbent article wearing area with favorable conditions for the growth of bacteria, this indicates that an undesirable environment favorable for the production of a bad odor or dermatitis (rash) by undesirable bacteria is also proceeded.

More specifically, bacteria producing a bad odor such as *Corynebacterium xerosis, Staphylococcus capitis*, etc. proliferate in the absorbent article wearing area. This generates an unwanted odor and increases the unpleasant sensation during wearing or replacing the absorbent article.

In addition, the growth of pathogenic microorganisms, such as *Propionibacterium acnes, Gardenerella vaginalis, Corynebacteruim minutissimum*, and *Staphylococcus aureus*, which may induce dermatitis or other diseases in the absorbent article wearing area, or the growth of microorganisms, such as *Propionibacterium avidum, Propionibacterium granulosum, Staphylococcus warneri*, and *Candida albicans*, causing infectious diseases not only increase the risk for the wearer to become afflicted with dermatitis and infectious diseases, but also may induce dermatitis or infectious diseases in the care persons or helpers.

In addition, the conditions under which such microorganisms proliferate involve an increase in the pH due to basic substances such as ammonia and amines produced by metabolism of the microorganisms, resulting in a decrease of function controlling the skin at a weakly acidic (pH4.5–6.5) inherently possessed by the skin. In addition, an increase in the pH make such circumstance that may cause a layer (or coating) of sebum, proteins, and amino acids in the outermost corneal layer of the epidermis which exhibits a barrier function and protects the skin to be easily removed.

In addition, an increase in the pH provides conditions in which microorganisms can easily grow. These act synergistically and a vicious circle is repeated. The environment to the human body continues to worsen.

As a technique for preventing proliferation of bacteria in the absorbent article wearing area, an absorbent article to which a quaternary ammonium salt such as benzalkonium (alkyldimethylbenzylammonium) chloride, cetylpyridinium chloride, or the like has been added as an antibacterial agent is disclosed in Japanese Patent Application Laid-open No. 1265/1990. This absorbent article, however, kills not only bacteria growing on the skin and causing contact dermatitis, but also bacteria useful to the human body due to inclusion of an antibacterial agent. As a result, the bacterial flora on the skin is changed so as to allow greater proliferation of harmful microorganisms which cause contact dermatitis. In addition, quaternary ammonium salts used as an antibacterial agent are cationic surfactant causing elution of sebum and natural moisturizing components which are present in the outermost corneal layer of the epidermis if an absorbent article is worn continuously for 24 hours. This may break down the barrier layer, accelerate permeation of body fluids and irritative chemical compounds into the skin, and adversely cause contact dermatitis.

SUMMARY OF THE INVENTION

An object of the present invention is therefore to solve the above problems in the conventional technology. Specifically, an object of the present invention is to provide an absorbent article such as a diaper and sanitary napkin which can prevent growth of undesirable bacteria producing a bad odor, dermatitis, infectious diseases, and the like on the skin surface of the wearer, thereby reducing the frequency of problem occurrences such as unpleasant odor and dermatitis (rash) when wearing such an absorbent article.

The present inventors have conducted extensive studies to achieve the above object and have found that if microorganisms in normal flora that are always present on the skin useful and/or harmless to the human body proliferate, growth of other microorganisms which are undesirable can be suppressed and the skin can be maintained in a clean state. The present inventors have conceived that, if this finding is applied to absorbent articles, the above problems can be solved.

Specifically, the present inventors have found that if the microorganisms in normal flora of the skin useful and/or harmless to the human body proliferate and the growth of undesirable microorganisms is suppressed in the absorbent article wearing area or inside the absorbent article, the above problems such as odor from the absorbent article and dermatitis (rash) on the wearer's skin can be reduced. This finding has led to the completion of the present invention.

The present inventors have further found that in order to cause only the microorganisms in normal flora of the skin useful and/or harmless to the human body to proliferate and to suppress the growth of other undesirable microorganisms, it is effective for the absorbent article to contain a compound assimilated only by the microorganisms in normal flora of the skin useful and/or harmless to the human body. This finding has also led to the completion of the present invention.

Therefore, the present invention relates to:

(1) An absorbent article comprising a compound assimilated only by a microorganism in the normal flora of the skin useful and/or harmless to the human body, (2) The absorbent article described in (1) above, wherein the microorganism of the skin useful and/or harmless to the human body is one or more microorganisms selected from the group consisting of lactic acid cocci, lactic acid bacilli, and monococci, (3) The absorbent article described in (1) or (2) above, wherein the compound assimilated only by the microorganism of the skin useful and/or harmless to the human body is a compound having an α1–2 glucose skeleton, and (4) The absorbent article described in (1) to (3) above, wherein the compound assimilated only by the microorganism of the skin useful and/or harmless to the human body is a glucooligosaccharide.

In the present invention, the effect of suppressing the growth of undesirable microorganisms by the microorganisms in normal flora of the skin useful and/or harmless to the human body can be explained as follows; the proliferation of the microorganisms is dependent on nutrition resources, water or moisture, oxygen, pH, and the like. However, because the amount of microorganisms grown in a given environment is limited, microorganisms grow antagonistically in that given environment. Therefore, under the conditions in which useful and/or harmless microorganisms easily grow, undesirable microorganisms are difficult to grow antagonistically.

The growth of a lactic acid coccus, lactic acid bacillus, or monococcus not only can suppress the growth of undesirable microorganisms, but can also discharge lactic acid by metabolism thereof. Therefore, the skin, as well as the surface and inside of absorbent article, is maintained in a weakly acidic state. The pH decrease can also maintain a clean environment. Furthermore, these microorganisms discharge lactic acid and urea by metabolism and increase the moisturizing effect of the skin.

As discussed above, in the present invention a compound assimilated only by microorganisms of the skin useful and/or harmless to the human body is contained in an absorbent article, such microorganisms on the skin useful and/or harmless to the human body can be selectively grown, and the growth of undesirable microorganisms can be controlled. As a result, the absorbent article of the present invention not only can prevent production of a bad odor by microorganisms, but also can prevent the skin suffering for a rash or the like.

DETAILED DESCRIPTION OF THE INVENTION

The present invention will be explained in more detail in the following description, which is not intended to be limiting of the present invention.

The absorbent article in the present invention includes disposal diapers for infants and adults, sanitary napkins, vaginal discharge liners, incontinence shorts, training pants, diaper holders, and vaginal insertion absorbent articles such as tampons, and the like.

These disposal diapers, sanitary napkins, and vaginal discharge liners have a basic structure comprising a permeable top sheet on the uppermost surface of the absorbent article, an absorber provided under the top sheet which absorbs and holds body fluids passing through the top sheet, and a back sheet provided outside the absorber which prevents the body fluids from leaking out.

The present invention is characterized by incorporating a compound assimilated only by microorganisms in the normal flora of the skin useful and/or harmless to the human body in the absorbent article and causing such microorganisms in the normal flora on the skin useful and/or harmless to the human body to selectively proliferate, thereby controlling the growth of undesirable microorganisms. Specifically, the present invention makes the best use of characteristics that the growth of any microorganisms is limited to a certain level, therefore, if microorganisms useful and/or harmless to the human body are selectively grown, the growth of the other microorganisms which are undesirable for the human body can be controlled adversely. The compound assimilated only by microorganisms in the normal flora of the skin useful and/or harmless to the human body may be referred to as "normal flora control agent" in the following description.

As examples of the microorganism in the normal flora of the skin useful and/or harmless to the human body, lactic acid bacteria such as lactic acid cocci and lactic acid bacilli, and monococci, can be given. A particularly preferable lactic acid bacterium is *Lactobacillus pentosus* and a particularly preferable monococcus is *Micrococcus kristinae*.

As a compound assimilated only by the microorganism in the normal flora of the skin useful and/or harmless to the human body, a compound having an α1–2 skeleton, such as glucooligosaccharide can be given. The α1–2 glucose skeleton can function as a substrate for the enzymes specifically possessed by lactic acid bacteria. Kojibiose is given as another compound having the α1-2 skeleton.

The normal flora control agent used in the present invention as the compound assimilated only by the microorganisms in the normal flora of the skin useful and/or harmless to the human body may be any material containing glucooligosaccharide, preferably a material containing 70 wt % or more glucooligosaccharide. For example, a commercially available glucooligosaccharide BIOECOLIA™ (manufactured by Nikko Chemicals Co., Ltd.) obtained by the immobilized enzyme method from sucrose or maltose which is natural saccharides can be conveniently used. BIOECOLIA™ contains 87% or more glucooligosaccharide.

Microorganisms in the normal flora of the skin useful and/or harmless to the human body easily proliferate in weakly acidic conditions. In this respect, the combined use of an organic acid with the absorbent article according to the preferred embodiment of the present invention is desirable to promote the growth of the normal flora of the skin useful and/or harmless to the human body.

As examples of the organic acid which can be used, citric acid, glycolic acid, tartaric acid, and lactic acid can be given.

In the present invention, the normal flora control agent such as glucooligosaccharide may be present in any one of the top sheet, absorber, or back sheet of the absorbent article, and is preferably applied to the top sheet or forms a composite with the absorber. In the case the normal flora control agent is applied to the surface of the top sheet coming into contact with the skin, the growth of microorganisms on the skin surface can be controlled. In the case such an agent forms a composite with the absorber, the growth of microorganisms in the body fluids absorbed in the absorber can be controlled.

When applying the normal flora control agent to the top sheet, an amount of 0.1–20 wt % of the weight of top sheet is used; if made into a composite with the absorber or the back sheet, an amount of 0.001–10 wt %, preferable 0.1–5 wt %, of the weight of the absorbent article is used.

A known any method such as coating, impregnation, and dipping is acceptable for forming a composite of the normal flora control agent and the absorber or back sheet. The normal flora control agent is dissolved or dispersed in an aqueous solvent such as water, propylene glycol, 1,3-butylene glycol, or glycerol, applied to an absorbent article or made into a composite, and dried.

To improve immobilization of the normal flora control agent on the absorbent article, an aqueous solution of a water-soluble polymer such as polyvinyl alcohol, sodium carboxymethylcellulose, polyethylene glycol, or polyacrylic acid can be used as a binder. A non-aqueous binder cannot exhibit the function of the present invention, because the non-aqueous binder disturbs transfer of the normal flora control agent to the skin.

There are no specific limitations to the top sheet to which the normal flora control agent is applied. Usually, such a sheet is a liquid permeable sheet-like material such as a non-woven fabric or permeable porous film.

The non-woven fabric used in the absorbent article is made of 1–5 d fiber and has 10–50 g/m$^2$. Fiber for non-woven fabric may be at least any one of synthetic fiber such as polyolefin and polyester, semi-synthetic fiber such as rayon, and natural fiber such as cotton, pulp, and silk.

The liquid permeable porous films used in the present invention are made from thermoplastics by extrusion, followed by boring using heated needles, embossing, hot blast, or the like. Polyethylene (density: 0.86–1.1 g/cm$^3$), polypropylene (density: 0.89–1.2 g/cm$^3$), and the like can be used either individually or in combination (i.e. either in single layer, multi-layer or mixed layer of those polymers) as the thermoplastics for porous films.

A permeable sheet material must permit body fluids to permeate and must withstand 0–300 mm H$_2$O of water pressure according to the JIS L1092 (Test method for water resistance of textiles, water resistance test method A (low water pressure method)). In addition, the permeable sheet material must have gas permeability to permit water vapor to pass through the surface material to the absorbent in the range of 5–700 cm$^3$/cm$^2$/sec according to the JIS L1906 (Test methods for non-woven fabrics made of filament yarn, Frazier type permeameter test method).

The above constitution of the absorbent article, in which a compound assimilated only by microorganisms in the normal flora of the skin useful and/or harmless to the human body is incorporated, ensures selective proliferation of microorganisms in the normal flora on the skin useful and/or harmless to the human body, whereby the growth of undesirable microorganisms can be controlled. As a result, in the present invention an odor produced by microorganisms in the absorbent article wearing area, or in the absorbent article, can be prevented, and the wearers and care persons are protected from dermatitis or infectious diseases due to microorganisms.

Furthermore, proliferation of microorganisms in the normal flora of the skin useful and/or harmless to the human body accelerates discharge of lactic acid by metabolism in the microorganisms. This maintains the surface of the skin, as well as the surface and inside of the absorbent article in an acidic state, in which the growth of undesirable microorganisms thus can be controlled.

Furthermore, discharge of lactic acid and urea by these microorganisms during metabolism increases the moisturizing effect of the skin.

Although the present invention is described in detail relating to absorbent articles such as disposal diapers, sanitary napkins and vaginal discharge liners in the above, the invention can also be applied to underwear shorts for incontinence, tampon, and the like.

EXAMPLES

The effect of controlling the growth of undesirable microorganisms by using a compound assimilated only by microorganisms in the normal flora of the skin useful and/or harmless to the human body in the absorbent article and causing such microorganisms in the normal flora on the skin useful and/or harmless to the human body to selectively proliferate will now be described by way of test examples (see the catalogue "BIOECOLIA" (February, 1997) of Nikko Chemicals, Co., Ltd.).

Test Example 1

Test Example 1 shows assimilation of glucooligosaccharide by various microorganisms.

The efficiency of digestion of glucooligosaccharide by various bacteria in the skin or vaginal mucous membrane was measured when the bacteria were cultivated for 48 hours in the presence of the glucooligosaccharide.

BIOECOLIA™ was used as the glucooligosaccharide.

BIOECOLIA™ contains 87% or more of glucooligosaccharide, 4% or less of glucose, and 4% or less of fructose. As a control, the efficiency of digestion of glucose was measured by cultivating the bacteria in the presence of the glucose under the same conditions as described above.

The efficiency of digestion in the Test Example 1 was scored as follows;

| Efficiency of digestion (%) | Score |
|---|---|
| 0–20 | – |
| 20–40 | + |
| 40–60 | ++ |
| 60–140 | +++ |

The results are shown in Tables 1, 2, and 3, which respectively show the efficiency of digestion by microorganisms in the normal flora of the skin, pathogenic bacteria, and infectious disease-related bacteria.

TABLE 1

| Microorganisms in the normal flora of the skin | BIOECOLIA ™ | Glucose |
|---|---|---|
| Lactobacillus pentosus (Useful bacteria, a kind of lactic acid bacteria) | +++ | +++ |
| Micrococcus kristinae (Useful bacteria, a kind of monococcus) | +++ | +++ |
| Corynebacterium xerosis (Bacteria producing a bad odor) | ++ | +++ |
| Staphylococcus capitis (A kind of Staphylococcus) | + | +++ |

TABLE 2

| Phatogenic bacteria | BIOECOLIA ™ | Glucose |
|---|---|---|
| Propionibacterium acnes (Acne bacteria) | – | +++ |

TABLE 2-continued

| Phatogenic bacteria | BIOECOLIA ™ | Glucose |
|---|---|---|
| Gardenerella vaginalis (A kind of bacteria) | − | + |
| Corynebacterium minutissimum (A kind of Bacillus diphtheriae) | − | +++ |
| Staphylococcus aureus (A kind of Staphylococcus) | − | +++ |

TABLE 3

| Bacteria which may induce infectious diseases | BIOECOLIA ™ | Glucose |
|---|---|---|
| Propionibacterium avidum (A kind of Propionibacteriaceae) | − | +++ |
| Propionibacterium granulosum (A kind of Propionibacteriaceae) | − | + |
| Staphylococcus warneri (A kind of Staphylococcus) | − | ++ |

The results of Table 1 have revealed that most microorganisms in normal flora of the skin useful for the human body can digest glucooligosaccharide. On the other hand, the results of Tables 2 and 3 indicate that almost no pathogenic bacteria nor bacteria which may induce infectious disease can digest glucooligosaccharide.

These results have thus proven that glucooligosaccharide can be selectively digested by the useful microorganisms in normal flora of the skin, but not by undesirable microorganisms such as pathogenic bacteria.

Test Example 2

Because the glucooligosaccharide has been shown to be selectively digested by the useful microorganisms in normal flora of the skin in the Test Example 1, the effect of glucooligosaccharide when two types of microorganisms were incubated together as a condition similar to the skin was tested in the Test Example 2.

As microorganisms, *Micrococcus kristinae* (useful microorganisms in normal flora) and *Staphylococcus aureus* and *Corynebacterium xerosis* (pathogenic bacteria) were used. These microorganisms were inoculated in a medium containing 0.5 g of BIOECOLIA™ and cultivated for 24 hours, whereupon the number of cells was counted to evaluate the effect of the glucooligosaccharide. (1) The results using the mixed bacterial system of *Micrococcus kristinae* (useful microorganisms in normal flora) and *Staphylococcus aureus* (pathogenic bacteria) are shown in Table 4.

TABLE 4

| The number of cells after 24 hours | The total number of cells | Staphylococcus aureus | Micrococcus kristinae (Useful microorganisms) |
|---|---|---|---|
| First test | $1 \times 10^8$ | $<1 \times 10^4$ | $>10^7$ |
|  | $1 \times 10^8$ | $<5 \times 10^4$ | $>10^7$ |
|  | $1 \times 10^8$ | $<5 \times 10^4$ | $>10^7$ |
| Second test | $1 \times 10^8$ | $<5 \times 10^4$ | $>5 \times 10^7$ |
|  | $5 \times 10^8$ | $<5 \times 10^4$ | $>5 \times 10^7$ |
|  | $5 \times 10^8$ | $<5 \times 10^4$ | $>5 \times 10^7$ |
| Third test | $1 \times 10^8$ | $<5 \times 10^4$ | $>10^7$ |
|  | $1 \times 10^8$ | $<5 \times 10^4$ | $>10^7$ |
|  | $1 \times 10^8$ | $<5 \times 10^4$ | $>10^7$ |

As shown in Table 4, the number of cells of useful bacteria has increased to ten times the number of cells at the start of the test, whereas the number of cells of pathogenic bacteria has decreased to about $\frac{1}{100}$. It can be seen from the above results that in this mixed bacterial system the useful *Micrococcus kristinae* can preferentially grow, whereas the growth of *Staphylococcus aureus*, which is a pathogenic bacterium, is inhibited.

(2) The results using the mixed bacterial system of *Micrococcus kristinae* (useful microorganisms in normal flora) and *Corynebacterium xerosisis* (pathogenic bacteria causing a bad odor) are shown in Table 5. In this test, $10^6$ cells were inoculated per 1 ml of the medium.

TABLE 5

| | Number of cells | | | |
|---|---|---|---|---|
| Bacteria | Initial | After 2 hours | After 6 hours | After 24 hours |
| Corynebacterium xerosis (Bacteria causing a bad odor) | $2.4 \times 10^6$ | $5.1 \times 10^5$ | $5.0 \times 10^5$ | $9.0 \times 10^4$ |
| Micrococcus kristinae (Useful microorganisms) | $2.4 \times 10^6$ | $8.2 \times 10^5$ | $3.1 \times 10^6$ | $5.1 \times 10^8$ |

It can be seen from the results shown in Table 5 that the useful *Micrococcus kiristinae* can preferentially grow in the presence of glucooligosaccharide, whereas the growth of odor-producing *Corynebacterium xerosis* is inhibited.

(3) The experiment was carried out in the same manner as in (2) above, except for inoculating $10^5$ cells per 1 ml of the medium. The results are shown in Table 6.

TABLE 6

| | Number of cells | | |
|---|---|---|---|
| Bacteria | Initial | After 6 hours | After 24 hours |
| Corynebacterium xerosis (Bacteria causing a bad odor) | $1.0 \times 10^5$ | $1.0 \times 10^4$ | $1.0 \times 10^5$ |
| Micrococcus kristinae (Useful microorganisms) | $1.0 \times 10^5$ | $5.0 \times 10^4$ | $1.0 \times 10^7$ |

It can be seen from the results shown in Table 6 that, also in the experiment inoculating a smaller number of cells, the useful *Micrococcus kristinae* can preferentially grow in the presence of glucooligosaccharide, whereas the growth of odor-producing *Corynebacterium xerosis* is inhibited.

The following examples, showing the experiments in which the findings of the above Test Examples 1 and 2 have been applied to absorbent articles, are given for the purpose of illustrating the present invention in more detail and should not be construed to be limiting the present invention.

EXAMPLE 1

The growth of bacteria in the absorbent article containing a normal flora control agent was examined.

[Preparation of Absorbent Article Sample]

A pad comprising a top sheet having liquid permeability, an absorber made from pulp and a high absorption resin capable of adsorbing and retaining body fluid, and a back sheet of polyethylene film was used as a sample of the absorbent article. The absorbent article was assembled from a top sheet material, an absorber, and a back sheet, while continuously supplying the top sheet material, which is a 25 g/m² non-woven fabric made from polyolefin fiber by melt-fusing. A 5% aqueous solution of BIOECOLIA™ in the amount of 20 g/m² was applied to the top sheet used for the absorbent article of the examples and dried, whereas no normal flora control agent was applied to the top sheet used for the absorbent article of the comparative example.

[Confirmation of the Growth of Bacteria]

Solutions containing 1×10⁵ cells of one of the following bacteria (i) to (v) per one ml were prepared. One ml of the solutions was applied to the absorbent articles of the examples and the comparative example respectively. The absorbent article samples were allowed to stand for 24 hours under the conditions of 35° C. and 95% RH. After 24 hours, each sample was extracted with sterile distilled water and cultivated in an agar medium. The number of living cells was counted. The results are shown in Table 7.

i: *Lactobacillus pentosus*
ii: *Micrococcus kristinae*
iii: *Staphylococcus aureus*
iv: *Corynebacterium xerosis*
v: *Propionibacterium avidum*

TABLE 7

|  | Useful bacteria | | Harmful bacteria | | |
| --- | --- | --- | --- | --- | --- |
|  | (i) | (ii) | (iii) | (iv) | (v) |
| Example | 5 × 10⁷ | 2 × 10⁸ | 4 × 10² | 8 × 10 | 6 × 10³ |
| Comparative Example | 2 × 10⁴ | 1 × 10³ | 8 × 10⁵ | 3 × 10⁴ | 2 × 10³ |

The results of Table 7 indicated proliferation of useful bacteria and a decrease of harmful bacteria by using glucooligosaccharide in the absorbent article.

EXAMPLE 2

A healthy adult wore the absorbent article of Example 1 for one week to examine itching and skin conditions in the absorbent article wearing area of the body after one week. The diaper was replaced five times every day. The adult wearing the absorbent article lived in a usual manner with respect to eating, bathing, going outside and so on.

The results are shown in Table 8.

TABLE 8

|  | Itching | Skin conditions |
| --- | --- | --- |
| Example | None | No change |
| Comparative Example | Itchy | Slight erythema |

The results of Table 8 show that no itching was sensed nor any change in the skin conditions was observed after wearing the absorbent article of the example containing glucooligosaccharide for one week, whereas skin itching was sensed and slight erythema was observed on the skin when wearing the absorbent article of the comparative example not containing glucooligosaccharide.

INDUSTRIAL APPLICABILITY

The present invention relates to an absorbent article comprising a compound assimilated only by microorganisms in the normal flora of the skin useful and/or harmless to the human body, and the microorganisms in the normal flora of the skin useful and/or harmless to the human body can be selectively proliferated in absorbent article wearing area, whereas the growth of undesirable microorganisms can be controlled. Therefore, the present invention is very useful as an absorbent article such as disposal diapers, sanitary napkins, vaginal discharge liners, incontinence shorts, training pants, diaper holders, and the like.

What is claimed is:

1. An absorbent atricle comprising a compound assimilated only by a microorganism in the normal flora of the skin, wherein the compound has an α 1–2-glucose skeleton.

2. The absorbent article of claim 1 wherein the microorganisms are selected from the group consisting of lactic acid cocci, lactic acid bacilli, and monococci.

3. The absorbent article of claim 1, wherein the compound is a glucooligosaccharide.

4. An aborbent article for placement next to skin comprising a device having an absorbent layer which is disposed on a surface of the device intended to be proximal to or in contact with the skin, said layer having disposed thereon or incorporated therein a compound that is selectively assimilated by a microorganism in the normal flora of the skin useful or harmless to the human body, wherein the compound has an α 1–2 glucose skeleton.

* * * * *